United States Patent [19]
Dormia

[11] Patent Number: 5,176,127
[45] Date of Patent: Jan. 5, 1993

[54] MANDREL FOR MEDICAL ENDOSCOPE

[76] Inventor: Enrico Dormia, Via Belvedere 35, Lecco, Italy

[21] Appl. No.: 646,561

[22] Filed: Jan. 28, 1991

[51] Int. Cl.[5] .............................................. A61B 1/32
[52] U.S. Cl. ............................................ 128/4; 128/3
[58] Field of Search ..................... 128/3, 4, 5, 6, 7, 8

[56]  References Cited

U.S. PATENT DOCUMENTS

| | | | |
|---|---|---|---|
| 1,602,233 | 10/1926 | Lyon | 128/7 |
| 1,624,716 | 4/1927 | Cerbo | 128/7 |
| 3,192,928 | 7/1965 | Horton | 128/3 |
| 3,496,930 | 2/1970 | Wappler | 128/5 |
| 3,720,203 | 3/1973 | Brown | 128/4 |
| 4,620,547 | 1/1986 | Boebel | 128/4 |
| 4,690,132 | 9/1987 | Bayer et al. | 128/4 |
| 4,756,313 | 7/1988 | Terwilliger | 128/4 |
| 4,782,818 | 11/1988 | Mori | 128/6 |
| 4,819,620 | 4/1989 | Okutsu | 128/4 |

FOREIGN PATENT DOCUMENTS 2418901  11/1982  Fed. Rep. of Germany.

Primary Examiner—Paul J. Hirsch
Attorney, Agent, or Firm—Kirschstein, Ottinger, Israel & Schiffmiller

[57]  ABSTRACT

Mandrel for medical endoscope having a mandrel head, consisting of elastic head segments which can be spread apart in a radial direction, with the outer edge of the jacket of the endoscope lying under the mandrel head being covered over by the outer edge of the segments which can be spread apart. Upon insertion of the endoscope, injuries due to the sharp edge of the jacket of the endoscope are avoided.

12 Claims, 2 Drawing Sheets

MANDREL FOR MEDICAL ENDOSCOPE

BACKGROUND OF THE INVENTION

1. Field of the Invention

The present invention relates to a mandrel for a medical endoscope.

2. Description of Related Art

As is known, medical endoscopes for examination or operation purposes, for example urological endoscopes, consist of a tubular outer jacket, into which an inner, rod-shaped, solid mandrel is introduced. The mandrel has a profiled mandrel head. Upon insertion of the endoscope, for example into a ureter of a patient, the profiled mandrel head projects out of the tubular jacket of the endoscope. The mandrel head is locked in this position of protrusion with respect to the tubular jacket of the endoscope using releasable securing means. The securing means are arranged on the end side of the endoscope jacket at its outer end lying opposite the insertion side. The profiled mandrel head, which projects from the tubular jacket, has the task of gradually widening the ureter during the process of insertion of the endoscope. In known endoscopes, the external diameter of the mandrel is kept slightly smaller than the internal diameter of the endoscope jacket. This results in the external diameter of the mandrel also being smaller than the external diameter of the endoscope jacket. This disadvantage is also to be found in endoscopes for performing surgical operations. These devices too have, at that end of the jacket of the endoscope to be inserted into the ureter for example, a profiled endpiece whose design is dependent on the operation to be performed. At that end of the endoscope jacket to be inserted, all known endoscopes form around the mandrel head a protruding edge, whose protrusion with respect to the mandrel head corresponds to the wall thickness of the endoscope jacket. Upon insertion of the endoscope, the border or the outer edge of the endoscope jacket leads inevitably to injuries to the ureter. When the endoscope is used for urological examinations, it is true that the injuries to the wall of the ureter scar over, but the scar formation is known to lead to narrowing of the ureter canal, and this often results in continuous pain and necessitates renewed surgical intervention.

The above designs for known urological endoscopes are also for endoscopes with mandrels which are to be inserted into further canals in the patient, and in which endoscopes, following insertion of the endoscope with the mandrel, the mandrel is subsequently withdrawn in order to insert into the jacket of the endoscope optical devices or electrically operated surgical appliances, for example electrically driven scalpels.

SUMMARY OF THE INVENTION

The aim of the invention is to propose a mandrel for endoscopes, which permits an insertion of the endoscope without risk of injury, i.e. without injuring the inside of the canal into the which the endoscope is inserted.

A further aim of the invention is to propose a mandrel suitable for endoscope jackets of different diameter.

In the case of a mandrel for endoscopes of the stated type, the aim is achieved according to the invention by virtue of the fact that a) the rod-shaped mandrel body is designed hollow, b) the profiled mandrel head has head segments which can be spread apart elastically in a radial direction from a rest position, in which the mandrel head is freely displaceable in the longitudinal direction in the jacket of the endoscope and a position for insertion of the endoscope into the canal of the patient, and in which position the external circumference of the mandrel head in the immediate vicinity of the endoscope jacket is essentially equal to the external circumference of the endoscope jacket, and by virtue of the fact that the head segments have internal spreading buffers, and c) a rod-shaped slide with spreading means is provided in the hollow mandrel body, and the spreading means cooperate with the spreading buffers belonging to the elastically deformable spreading segments and arranged in the mandrel head.

Further features of the mandrel according to the invention for medical endoscopes are given in the subclaims and in the description which now follows.

Important advantages are afforded by the mandrel for a medical endoscope as designed according to the invention. Thus, it is possible to carry on using the existing tubular jacket of known endoscopes without modification. The insertion of the endoscope into the canal of the patient takes place without any risk of injury, i.e. without damaging the inner wall of, for example, a ureter.

The insertion of the endoscope takes place with a quick and unimpeded sliding movement. The known components for securing and for releasing the displaceable insert piece in the tubular jacket of the endoscope, for axial positioning, remain unchanged. According to the invention, the elastically deformable mandrel head permits the insertion of any desired size of endoscope. It follows from this that the mandrels according to the invention can also be used for already existing, conventional endoscopes. It is therefore possible, in the case of conventional, known endoscopes, to replace the previously used mandrel with a new mandrel according to the invention. For the already existing endoscopes, no constructional modifications are necessary in respect of the optical ancillary devices or surgical devices.

A further advantage of the mandrel according to the invention lies in the fact that the individual segments of the mandrel head have a profile or shape which take account of both the thickness of the jacket wall and the design of the end of the jacket of the endoscope.

Following insertion of the endoscope with the mandrel head spread out, a withdrawal of the mandrel head is carried out by means of the mandrel head being decreased in diameter, this decrease taking place according to the invention quickly and reliably using the elasticity of the spreadable segments of the mandrel head.

A further advantage of the mandrel according to the invention lies in the fact that it can be re-used. In the case of mandrels with replaceable mandrel heads, it is advantageous if the same mandrel body and slide can be used for a multiplicity of different endoscopes with different dimensions. In this case, the slides can be connected to mandrel heads of different shape. A further advantage of the invention lies in the fact that one and the same mandrel head can also be used for endoscopes with different dimensions. In this case, the extent of the widening can be achieved by means of different axial lengths of stroke of the mandrel, for example using a setting thread.

Further features and advantages of the mandrel according to the invention for an endoscope for medical use can be taken from the description which now follows and from the attached drawings and the subclaims.

A BRIEF DESCRIPTION OF THE DRAWING

The subject of the invention is now described on the basis of exemplary embodiments and is shown in the drawings, in which.

For greater clarity, the individual components are shown on different scales in relation to one another.

A DETAILED DESCRIPTION OF THE PREFERRED EMBODIMENTS

Figure 1:
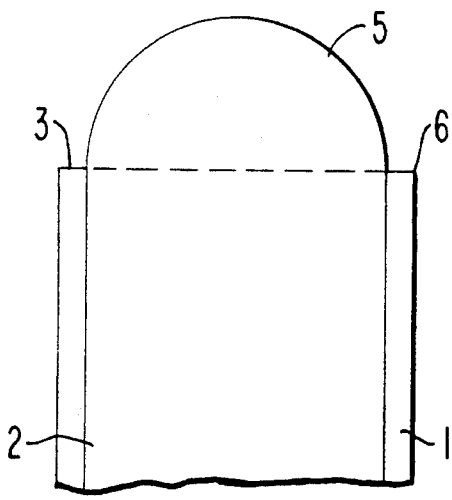
FIGS. 1 and 2 are a representation of the insertion part of two endoscopes with known mandrels, which are arranged in the jacket of the endoscope in the insertion position.
Figure 2:
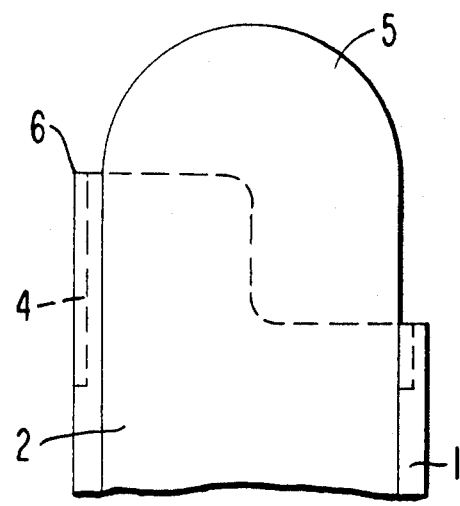
Figure 3:
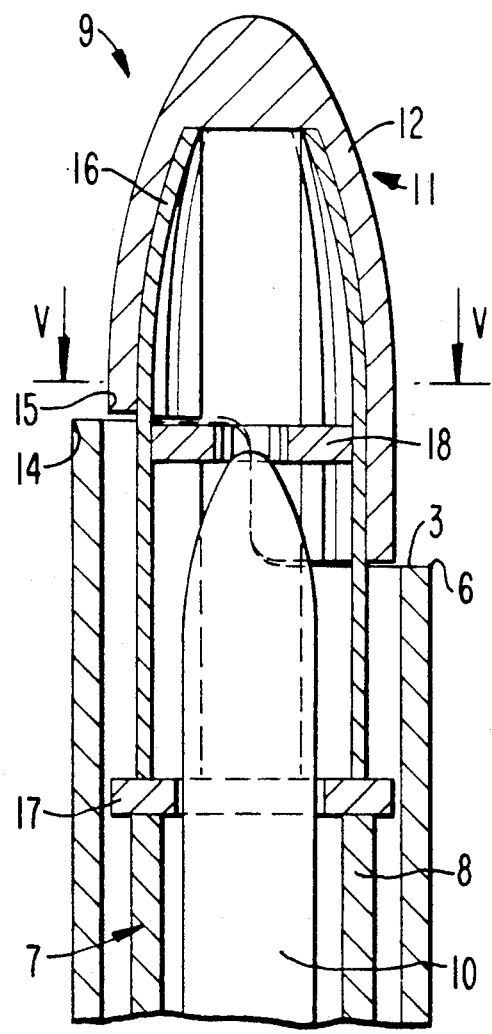
FIG. 3 is a longitudinal section through the insertion end part of an endoscope with a mandrel according to the invention in the non-spread state.
Figure 4:
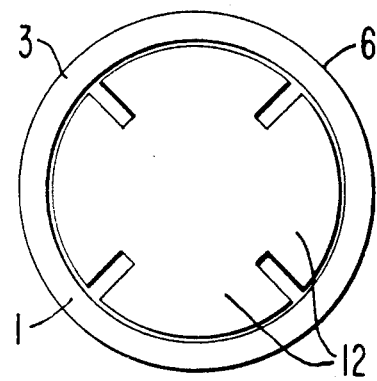
FIG. 4 is a plan view of the endoscope with a mandrel according to FIG. 3.

FIGS. 1 and 2 the insertion head end of the jacket of a medical endoscope is shown by 1. The mandrel is indicated by 2. In FIG. 1, the end 3 of the jacket is designed plane and perpendicular to the longitudinal axis of the jacket 1; in FIG. 2, in contrast, the end 1 is defined by a profiled circumferential line 4 which is indicated with broken lines. Endoscopes often have different designs of jacket end piece, depending on the medical operations to be performed. A common feature of the known endoscopes is that they receive a solid mandrel 2 whose end 5 at the side to be inserted is of rounded design. The jacket 1 of the endoscope has an exposed protruding circumferential edge 6. Means (not shown) are also provided for positional securing of the mandrel 2 in the inside of the jacket 1 in the position of insertion of the endoscope into the corresponding canal in the patient, for example into a ureter. Following insertion of the endoscope 1, the mandrel 2 is removed from the tubular jacket, in order to permit the introduction of an optical or a surgical device into the jacket 1.

In order to avoid damage due to the protruding edge 6 of the jacket 1, according to the invention the mandrel 7 is designed as a tube 8 which supports, at its end, a mandrel head 9 which is designed such that it can be spread radially and is provided with a rod-shaped slide 10 for the spreading procedure. Arranged at the actuation side of the mandrel 7 are coupling facilities which are known per se and co-operate with the tubular jacket 1 of the endoscope, these coupling facilities are known and are not illustrated. The end of the rod-shaped slide 10 projects from the jacket 1 and can be gripped by the operating surgeon, in order to carry out the axial displacement of the slide in a controlled manner.

Figure 5:
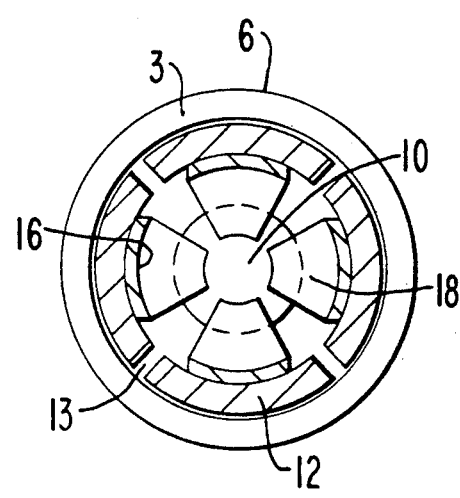
FIG. 5 is a cross-section following line V—V in FIG. 3.
Figure 6:
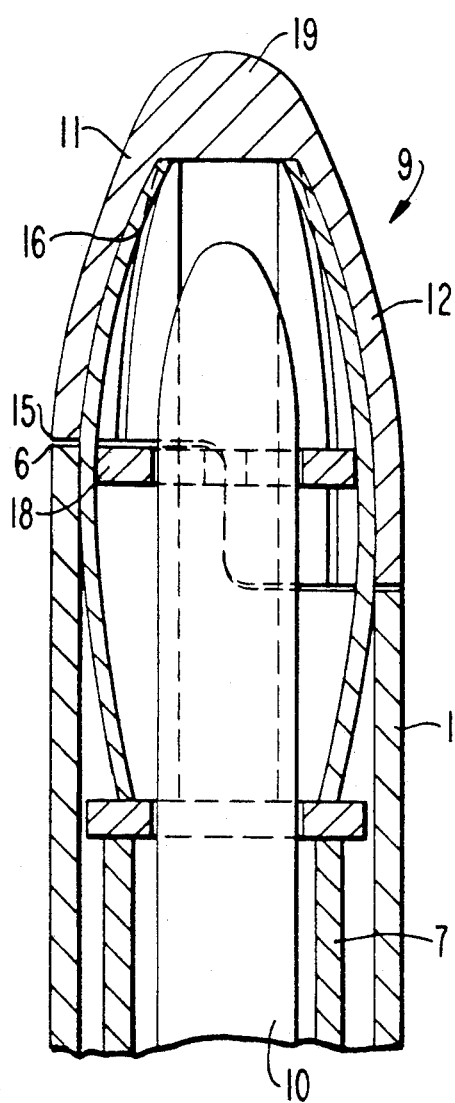
FIG. 6 is a section similar to FIG. 3, with the mandrel spread out, i.e. with the endoscope ready for the insertion procedure.
Figure 7:
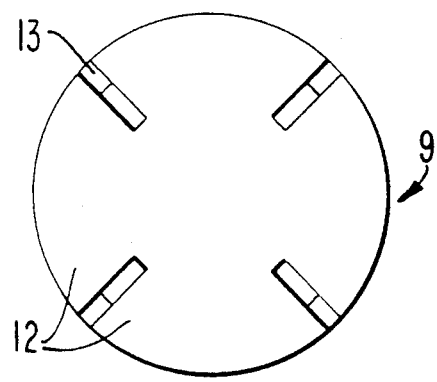
FIG. 7 shows a plan view of the endoscope with mandrel according to FIG. 6.

The spreadable head 9 has a tapering shape and the wall 11 of the mandrel head is, in the illustrated example, divided into four head segments 12 which are separated from each other by longitudinal slots 13. With the mandrel 7 inserted in the insertion state in the jacket 1 of the endoscope, the lower side 14 of the segments 12 has a course which corresponds essentially to the course of the tubular jacket 1 of the endoscope. In this connection, the segments are distanced from the underlying jacket 1; in this way the segments 12 can be spread radially outwards until their outer circumferential edge 15 comes to cover the underlying edge 6 of the jacket 1 of the endoscope. In order to do this, in the embodiments according to FIGS. 3 to 8 a strip 16 of elastic material, for example spring steel, is arranged on the inner side of each of the segments 12. The strips 16 extend in an axial direction under the wall parts of the segments 12 towards the tubular body 8 of the mandrel 7. The strips 16 are secured to the tubular body 8, for example by means of welding and with interposition of a collar 17. As buffers for the means for spreading the elastic segments 16, inner buffers 18 are provided, which protrude radially inwards in such a way that, upon a radially outward directed displacement movement, the positional arrangement of the circumferential edge 15 of the segments 12 is essentially congruent with the underlying circumferential edge 6 of the jacket 1. According to the invention, the radial outward displacement of the segments 12 is achieved using the rod-shaped slide 10, which for this purpose has a pointed end and exhibits an external diameter which, after carrying out the spreading stroke, as illustrated in FIGS. 5 and 6, causes an essentially radially outward directed spreading of the segments 12 of the head 9. In this position, the outer circumferential edge 6 of the tubular jacket 1 of the endoscope does not constitute a sharp edge, which could lead to injuries, since the edge 6 is covered by the external circumference of the mandrel head 9 of essentially equal diameter. After spreading out of the mandrel head 9, the endoscope can be inserted without difficulties into a canal, for example into the ureter of a patient, without any risk of injury, and this even in the case of endoscopes of relatively large diameter. In the spread-out position, the circumference of the mandrel head can be slightly smaller or slightly larger compared to the external circumference of the endoscope jacket, depending on the type of endoscope to be used.

After inserting the endoscope with the spread-out mandrel head 9, for example into the bladder of the patient, without causing any injury, the mandrel 10 is pulled out simply after withdrawing the rod-shaped slide 10. This results in the elastic segments 16 springing back from their spread position into their initial position, utilising their intrinsic elasticity. After this radially inward directed spring-back movement (FIG. 3), the tube 8 is disengaged from the jacket 1 of the endoscope and the mandrel is pulled out in a known manner.

In the above description, no details were given of the thickness of the segments 12 which can be spread apart, or of the thickness of the elastically deformable segments 16 and of the internal buffers 18 for the spreading apart, since these components can have different dimensions. It should be noted that the difference in diameter between the external diameter of the rod-shaped slide 10 and the internal diameter or the minimum distance between the internal buffers 18 is essentially equal to the wall thickness of the jacket 1 of the endoscope. It should also be pointed out that, with the mandrel head 9 situated in the rest position, i.e. upon insertion or withdrawal thereof from the tubular jacket 1 of the endoscope, the external circumference of the outermost circumferential edge 15 must be smaller than the internal circumference of the jacket 1 of the endoscope, in order thereby to permit an axial movement between the jacket 1 of the endoscope and the mandrel.

It should also be pointed out that the small partial areas of the outer edge 6, which remain free in accordance with the longitudinal slots 13, are also small in the case of the spread-out mandrel head, in such a way that no risk of injury need be feared.

With the described construction, which can be set up in a simple manner using conventional manufacturing methods, it is possible for the lower side 14 of the protruding sectors 12 of the mandrel head, which can be spread out, to be given any desired shape.

Figure 8:
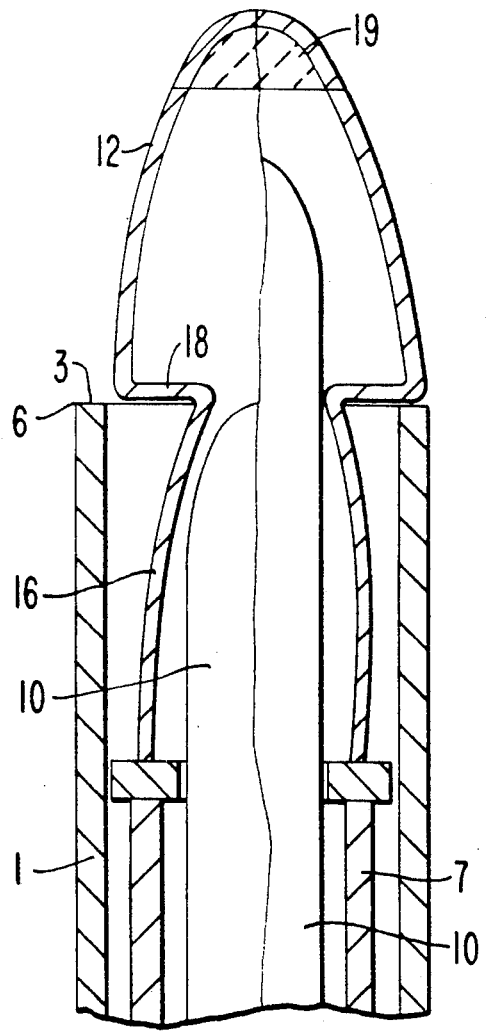
FIG. 8 shows a longitudinal section through the insertion end part of an endoscope in a modified embodiment of the mandrel, in which the mandrel is shown prior to the spreading procedure on the left-hand side of the drawing and following the spreading procedure on the right-hand side.

In the example according to FIG. 8, the spreadable head 9 of the mandrel 7 is made up of profiled head segments 12, which are obtained directly from strip-shaped, elastic components 16. An internal spreading buffer 18 is moreover formed on these head segments by means of bending. As in the previously described exemplary embodiment, the strip-shaped segments 16 can be secured at their lower side in a collar 17 and can be connected at their upper side with a tapering cap 19. As in the previously described example, four strip-shaped segments 12 and 16 can be provided. However, these segments can also be provided in any desired number.

The design of the buffers 18 in the manner of circular segments, as illustrated in FIGS. 3 to 7, and in the form of folds, as illustrated in FIG. 8, can be modified as desired. It is sufficient if the basic features and previously mentioned structural features are retained.

In practice, the mandrels according to the invention have an external diameter of the collar 17 or the tubular body similar to the external diameter of conventional mandrels of solid design. The mandrels according to the invention can therefore also be used at any time in jackets of already existing endoscopes. The mandrel according to the invention must merely have a spreadable head of appropriate shape.

It also comes within the area of protection of the present invention if replaceable, spreadable heads are used for the same tubular mandrel body. The replaceability of the spreadable heads is obtained, for example, by virtue of the fact that a releasable connection, for example via a thread, is provided between the collar 17 and the tubular body 8 of the mandrel. The collar 17 then advantageously has a design in the manner of a nut.

It further comes within the area of protection of the present invention to use mandrels with spreadable heads, which are used for endoscope jackets of different diameter. For this purpose, a head according to FIG. 8 can be used, which head can execute a long spreading stroke in a radial direction. The rod-shaped slide of the mandrel in this case has a conically shouldered endpiece of considerable length. Thus, it is possible to carry out a fine adjustment of the radial spreading stroke as a function of the axial stroke of the rod-shaped slide. This stroke with fine adjustment can be effected at the end of the rod-shaped slide, for example by means of an adjustment thread and a setting nut, which is not described further.

Although the preferred material for producing the elastically designed segments of the mandrel head was stated to be spring steel, in practice the materials and the dimensions as well as the shape of the individual components of the mandrel can be freely chosen.

The area of protection of the present invention includes, in addition to the mandrels which can be spread out, endoscopes which are equipped with these spreadable mandrels.

I claim:

1. A mandrel for atraumatically inserting into a body cavity an elongated tubular endoscopic jacket having an open end bounded by a jacket edge, said mandrel comprising:
    (a) a hollow mandrel tube extending along a longitudinal axis within and along the jacket;
    (b) a mandrel head on the tube exteriorly of the jacket, said head having a blunt leading end region, a trailing end region, and a plurality of elastic head segments spaced around the longitudinal axis and extending between the leading and trailing end regions; and
    (c) means for spreading the head segments apart from one another radially of the longitudinally axis from an upspread position in which the head passes with clearance through the tube, to a spread position in which the trailing end region of the head overlies the jacket edge to resist injury to the body cavity during insertion of the jacket, said spreading means including
        (i) a push rod mounted in the tube for sliding movement along the longitudinal axis, and
        (ii) projections spaced around the longitudinal axis and connected to the head segments, said projections extending into the path of movement of the push rod to radially move the head segments upon movement of the push rod.

2. The mandrel according to claim 1, wherein the open end of the jacket lies in a first plane generally perpendicular to the longitudinal axis, and wherein the trailing end region of the head lies in a second plane generally parallel to said first plane.

3. The mandrel according to claim 1, wherein the open end of the jacket is stepped and has jacket end portions lying in a first set of offset planes generally perpendicular to the longitudinal axis, and wherein the trailing end region of the head has head end portions lying in a second set of offset planes generally parallel to said first set.

4. The mandrel according to claim 1, wherein the head has an interior space into which the tube extends.

5. The mandrel according to claim 1, wherein the segments are separated by longitudinal slits equiangularly arranged about the longitudinal axis.

6. The mandrel according to claim 1, wherein the push rod has a blunt leading rod end, and wherein the projections bound an open circular zone through with the blunt leading rod end moves.

7. The mandrel according to claim 1, wherein each projection has a sector shape.

8. The mandrel according to claim 1, wherein the projections and head segments are constituted of metal, and wherein the projections are individually welded to the head segments.

9. The mandrel according to claim 1, wherein the tube, the head, and the spreading means are each constituted of metal.

10. The mandrel according to claim 6, wherein the jacket has a side wall of a predetermined radial thickness, wherein the push rod has a predetermined diameter, and wherein the open circular zone has a predetermined diametral dimension; and wherein the difference between the predetermined diameter and the predetermined diametral dimension is generally equal to said predetermined radial thickness.

11. The mandrel according to claim 1, wherein the head is constituted of spring steel.

12. The mandrel according to claim 1, wherein the head is integral with the tube.

* * * * *